United States Patent
Kerl et al.

(10) Patent No.: US 10,080,716 B2
(45) Date of Patent: *Sep. 25, 2018

(54) PACKAGING UNIT HAVING PARTICULAR AMINATED SILICONE POLYMER

(71) Applicant: Henkel AG & Co. KGaA, Duesseldorf (DE)

(72) Inventors: Sylvia Kerl, Hamburg (DE); Susanne Bietz, Elmshorn (DE)

(73) Assignee: Henkel AG & Co. KGaA (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/454,106

(22) Filed: Mar. 9, 2017

(65) Prior Publication Data
US 2017/0172901 A1    Jun. 22, 2017

Related U.S. Application Data
(63) Continuation of application No. PCT/EP2015/068876, filed on Aug. 18, 2015.

(30) Foreign Application Priority Data

Sep. 9, 2014 (DE) .................. 10 2014 218 006

(51) Int. Cl.
*A61Q 5/10* (2006.01)
*A61K 8/898* (2006.01)
*A61K 8/06* (2006.01)
*A61K 8/22* (2006.01)

(52) U.S. Cl.
CPC ............ *A61K 8/898* (2013.01); *A61K 8/062* (2013.01); *A61K 8/22* (2013.01); *A61Q 5/10* (2013.01); *A61K 2800/4322* (2013.01); *A61K 2800/4324* (2013.01); *A61K 2800/48* (2013.01); *A61K 2800/87* (2013.01); *A61K 2800/88* (2013.01); *A61K 2800/882* (2013.01)

(58) Field of Classification Search
CPC .......... A61Q 5/10; A61Q 5/065; A61K 8/898; A61K 8/415; A61K 8/41; A61K 8/347; A61K 2800/4324; A61K 2800/88; A61K 2800/882
See application file for complete search history.

(56) References Cited

U.S. PATENT DOCUMENTS

| | | | |
|---|---|---|---|
| 6,596,035 B2 * | 7/2003 | Gutkowski ............ | A61K 8/22 8/110 |
| 2003/0152534 A1 * | 8/2003 | Legrand ................ | A61K 8/35 424/61 |
| 2003/0229947 A1 | 12/2003 | Clarke et al. | |
| 2014/0190999 A1 * | 7/2014 | Weser ................... | A61K 8/42 8/405 |

FOREIGN PATENT DOCUMENTS

| | | |
|---|---|---|
| EP | 1426038 A1 | 6/2004 |
| FR | 2945731 A1 | 11/2010 |
| WO | 02/47632 A2 | 6/2002 |
| WO | 03/009822 A2 | 2/2003 |
| WO | 2012/079915 A2 | 6/2012 |

OTHER PUBLICATIONS

STIC Search Report dated May 9, 2017.*
PCT International Search Report (PCT/EP2015/068876) dated Oct. 13, 2015.
Liu X. M. et. al.; "Comparative Studies of Poly(DimethylSiloxanes) Using Automated GPC-MALDI-TOF MS and On-Line GPC-ESI-TOF MS"; Am. Soc. Mass. Spectrom., 2003, 14, 195-202.

* cited by examiner

*Primary Examiner* — Eisa B Elhilo
(74) *Attorney, Agent, or Firm* — P. Scott Smith

(57) ABSTRACT

A packaging unit (kit of parts) for dyeing keratin fibers and related methods. The packaging unit includes, formulated separately from one another, at least one container (C1), comprising a cosmetic agent (M1), which comprises at least one compound, selected from oxidation dye precursors, direct dyes and the mixtures thereof, and at least one aminated silicone polymer, comprising at least one structural unit of formula (I) and at least one structural unit of formula (II)

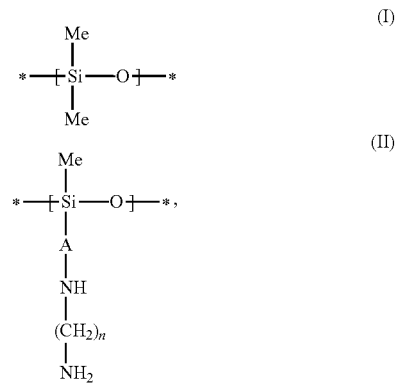

where a denotes a linear or branched $C_4$ to $C_8$ alkyl group; and n denotes integers from 1 to 4. The kit further comprises at least one container (C2) including an oxidizing agent preparation (M2), which, in a cosmetically compatible carrier, comprises at least one oxidizing agent in a total amount of 0.5 to 15 wt. % based on the total weight of the oxidizing agent preparation.

18 Claims, No Drawings

PACKAGING UNIT HAVING PARTICULAR AMINATED SILICONE POLYMER

FIELD OF THE INVENTION

The present invention relates to a packaging units (kit of parts), including a cosmetic agent comprising specific aminated silicone polymers and an oxidizing agent preparation.

The present invention furthermore relates to a method for coloring keratin fibers using a packaging unit according to the invention.

Finally, the present invention relates to the use of a packaging unit according to the invention for producing a cosmetic agent for altering the color of keratin fibers, providing increased nourishment of the keratin fibers and/or improved chroma of color nuances.

BACKGROUND OF THE INVENTION

Altering the shape and the color of hair represents an important field of modern cosmetics. This allows the appearance of the hair to be adapted both to current fashion trends and to the individual desires of the particular consumer. The color design of hair styles in keeping with fashion or covering of graying or white hair with trendy or natural hues is usually carried out using color-altering agents. In addition to a high coloring performance, these agents are to have additional properties, such as to increase the hair volume.

Various dyeing systems are known in the prior art for providing color-altering cosmetic agents, in particular for the skin or for keratin-containing fibers, such as human hair.

Oxidation dyes are used for permanent, intensive colorations having appropriate fastness properties. Such dyes typically include oxidation dye precursors, referred to as developer components and coupler components. Under the influence of oxidizing agents or atmospheric oxygen, the developer components develop the actual dyestuffs among each other or by coupling to one or more coupler components. The oxidation dyes are characterized by outstanding, long lasting coloring results. For naturally appearing colorations, however, usually a mixture of a larger number of oxidation dye precursors are used; in many instances, direct dyes continue to be used for nuancing.

Permanent or semi-permanent coloring agents including what are known as direct dyes as the coloring component are typically used for temporary colorations. These are dye molecules that attach directly to the substrate and require no oxidative process to develop the color. Henna, which is already known for coloring the body and hair from ancient times, belongs to these dyes, for example. In general, these colorations are considerably more sensitive to shampooing than oxidative colorations, so that in many instances an undesirable shift in the nuance, or a visible homogeneous loss of color, takes place much earlier.

Finally, another dyeing method has attracted great interest. In this method, precursors of the natural hair pigment melanin are applied to the substrate, such as the hair; these precursors then develop nature-analogous dyes as part of oxidative processes in the hair. Such methods use 5,6-dihydroxyindoline as the dye precursor, for example. In particular, when using agents comprising 5,6-dihydroxyindoline multiple times, it is possible to restore the natural hair color of people having grayed hair. The dyeing result may be achieved using atmospheric oxygen as the only oxidizing agent, whereby additional oxidizing agents can be dispensed with. In people having originally ash blond to brown hair, 5.6-dihydroxyindoline may be used as the sole dye precursor. In contrast, satisfactory results in the use on people having originally a red, and in particular a dark to black, hair color, can frequently only be achieved by simultaneously using additional dye components, and more particularly special oxidation dye precursors.

The dyes known from the prior art, however, do not always result in the desired high coloring performance or do not have any adequate additional desirable properties, such as improved nourishment of the hair during dyeing of the hair.

BRIEF SUMMARY OF THE INVENTION

It was therefore the object of the present invention to provide a cosmetic agent for dyeing keratin fibers which avoids or at least mitigates the disadvantages of the state of the art, and which results in improved nourishment of the hair and/or improved chroma of the color nuances, which is to say an increased chroma number.

Furthermore, other desirable features and characteristics of the present invention will become apparent from the subsequent detailed description of the invention and the appended claims, taken in conjunction with this background of the invention.

A first subject matter of the invention is thus a packaging unit (kit of parts) for coloring keratin fibers, comprising, formulated separately from one another, a) at least one container (C1), comprising a cosmetic agent (M1), which comprises at least one compound, selected from the group consisting of oxidation dye precursors, direct dyes and the mixtures thereof, and at least one aminated silicone polymer, comprising at least one structural unit of formula (I) and at least one structural unit of formula (II)

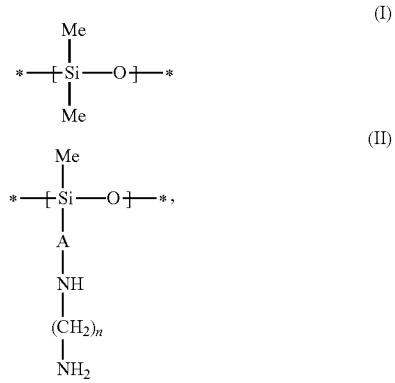

where
A denotes a linear or branched $C_4$ to $C_8$ alkyl group; and
n denotes integers from 1 to 4, b) at least one container (C2), comprising an oxidizing agent preparation (M2), which, in a cosmetically compatible carrier, comprises at least one oxidizing agent in a total amount of 0.5 to 15 wt. %, especially of 0.75 to 10 wt. %, preferably of 1 to 7.5 wt. %, particularly preferably of 1.25 to 7 wt. %, and in particular of 1.5 to 6.0 wt. %, based on the total weight of the oxidizing agent preparation.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Surprisingly, it was now found that the use of at least one specific aminated silicone polymer is cosmetic agents, which represent a component of a packaging unit (kit of parts), results in improved nourishment of keratin fibers and/or improved chroma of the color nuances. One indicator of improved nourishment is increased combability, especially wet combability, while one indicator of improved chroma of color nuances is an increased chroma number. As a result of the use according to the invention of at least one specific aminated silicone polymer, a higher chroma number and/or improved wet combability are achieved.

According to the above formulas and all formulas provided hereafter, a chemical bond identified by the "*" symbol denotes a free valence of the corresponding structure fragment. Free valence here shall be understood to mean the number of atom bonds originating from the corresponding structure fragment at the position identified with the "*" symbol. Within the scope of the present invention, preferably a respective atomic bond extends from the positions of the structure fragments identified by the "*" symbol to further structure fragments.

According to the invention, the term "keratinic fibers or keratin fibers" shall be understood to mean furs, wool, feathers, and human hair. Within the scope of the present invention, it is particularly preferred when the cosmetic agents are used to color human hair.

Moreover, the term "container" within the scope of the present invention shall be understood to mean an enclosure present in the form of an optionally re-closable bottle, a tube, a can, an envelope, a sachet or similar enclosures. There are no limits according to the invention as to the material of the enclosure. Preferably, however, these are enclosures made of glass or plastic material.

Moreover, the term "aminated silicone polymers" within the scope of the present invention shall be understood to mean silicone polymers that comprise at least one amino group per silicone polymer.

Furthermore, the term "combability" within the scope of the present invention shall be understood to mean both the combability of the wet fiber and the combability of the dry fiber.

In addition, the term "fatty alcohols" within the scope of the present invention shall be understood to mean aliphatic, long-chain, monohydric, primary alcohols that include unbranched hydrocarbon residues having 6 to 30 carbon atoms. The hydrocarbon residues may be saturated, or monounsaturated or polyunsaturated.

Finally, the term "fatty acids" within the scope of the present invention shall be understood to mean aliphatic monocarboxylic acids having an unbranched hydrocarbon carbon chain, which comprises hydrocarbon residues having 6 to 30 carbon atoms. The hydrocarbon residues may either be saturated, or monounsaturated or polyunsaturated.

Unless indicated otherwise, the information regarding the total amount with respect to the components of the cosmetic agent (M1) in the present invention refers to the total amount of active substance of the particular component. Furthermore, unless indicated otherwise, the information regarding the total amount with respect to the components of the cosmetic agent refers to the total weight of the oxidizing agent-free cosmetic agent according to the invention.

The cosmetic agents (M1) in the container (C1) comprise a cosmetic carrier. According to the invention, the cosmetic carrier is preferably aqueous, alcoholic or aqueous-alcoholic. Within the scope of the present invention, creams, emulsions, gels, or surfactant-containing foaming solutions, for example, such as shampoos, foam aerosols or other preparations, which are suitable for use on hair, can be used.

An aqueous carrier within the meaning of the invention comprises at least 30 wt. %, and in particular at least 50 wt. %, water, based on the total weight of the cosmetic agent (M1).

Aqueous-alcoholic carriers within the meaning of the present invention shall be understood to mean compositions including water and a total amount of 3 to 90 wt. % of a C1-C4 alcohol, based on the total weight of the cosmetic agent (M1), in particular ethanol or isopropanol.

The cosmetic agents (M1) in the container (C1) may additionally include further organic solvents, such as methoxybutanol, ethyldiglycol, 1,2-propylene glycol, n-propanol, n-butanol, n-butylene glycol, glycerol, diethylene glycol monoethyl ether, and diethylene glycol mono-n-butyl ether. All water-soluble organic solvents are preferred, wherein the solvent is present in a total amount of 0.1 to 30 wt. %, especially 1 to 20 wt. %, and in particular 2 to 10 wt. %, based on the total weight of the cosmetic agent (M1).

The cosmetic agent (M1) in the container (C1) comprises a compound selected from the group consisting of oxidation dye precursors (ODP), direct dyes (DD), and the mixtures thereof, as the first essential component.

In a preferred embodiment, cosmetic agents (M1) in the container (C1) comprise at least one oxidation dye precursor.

Oxidation dye precursors can be divided into two categories based on the reaction behavior thereof, these being developer components and coupler components. Developer components are able to form the actual dyestuff on their own. They may thus be present as sole compounds in the cosmetic agent according to the invention. In a preferred embodiment, the cosmetic agents (M1) in the container (C1) thus comprise at least one oxidation dye precursor of the developer type. However, it may also be provided within the scope of the present invention that the cosmetic agents (M1) comprise at least one oxidation dye precursor of the coupler type. Particularly good results with respect to the coloration of keratin fibers are obtained when the cosmetic agents (M1) comprise at least one oxidation dye precursor of the developer type and at least one oxidation dye precursor of the coupler type.

The developer and coupler components are typically used in the free form. However, it may be preferred to use the salt form in the case of substances comprising amino groups, and in particular in the form of the hydrochlorides and hydrobromides or the sulfates.

According to the invention, preferred cosmetic agents (M1) are those that comprise the developer component and/or the coupler component each in a total amount of 0.001 to 10 wt. %, especially 0.01 to 8 wt. %, preferably 0.1 to 5 wt. %, and in particular 0.5 to 3 wt. %, based on the total weight of the antiperspirant cosmetic agent (M1).

In a further preferred embodiment, the cosmetic agent (M1) in the container (C1) is thus characterized by comprising an oxidation dye precursor of the developer type and/or of the coupler type in a total amount of 0.001 to 10 wt. %, especially 0.01 to 8 wt. %, preferably 0.1 to 5 wt. %, and in particular 0.5 to 3 wt. %, based on the total weight of the cosmetic agent (M1).

Suitable oxidation dye precursors of the developer type are n-phenylenediamine and the derivatives thereof, for example. Preferred p-phenylenediamines are selected from one or more compounds of the group consisting of p-phenylenediamine, p-toluylenediamine, 2-chloro-p-phenylenediamine, 2,3-dimethyl-p-phenylenediamine, 2,6-dimethyl-p-phenylenediamine, N,N-bis-(2-hydroxyethyl)-p-phenylenediamine, 2-2-hydroxyethyl)-p-phenylenediamine, 2-(1,2-dihydroxyethyl)-p-phenylenediamine, N-(2-hydroxypropyl)-p-phenylenediamine, N-(4'-aminophenyl)-p-phenylenediamine, 2-methoxymethyl-p-phenylenediamine, N-phenyl-p-phenylenediamine, 2-(2-hydroxyethyloxy)-p-phenylenediamine, and N-(4-amino-3-methyl-phenyl)-N-[3-(1H-imidazole-1-yl)propyl]amine, and the physiologically compatible salts thereof.

It may furthermore be preferred according to the invention to use compounds comprising at least two aromatic nuclei that are substituted with amino groups and/or hydroxyl groups as the developer component. Preferred binuclear developer components are selected from N,N'-bis-(2-hydroxyethyl)-N,N'-bis-(4'-aminophenyl)-1,3-diamino-propan-2-ol, N,N'-bis-(4-aminophenyl)-1,4-diazacycloheptane, bis-(2-hydroxy-5-aminophenyl)methane, and the physiologically compatible salts thereof.

It may furthermore be preferred according to the invention to use a p-aminophenol derivative or one of the physiologically compatible salts thereof as the developer component. Preferred p-aminophenols are p-aminophenol, N-methyl-p-aminophenol, 4-amino-3-methylphenol, 4-amino-2-aminomethylphenol, 4-amino-2-(1,2-dihydroxyethyl)phenol, 4-amino-2-(diethylaminomethyl)phenol, and the physiologically compatible salts thereof.

The developer component may furthermore be selected from o-aminophenol and the derivatives thereof, preferably from 2-amino-4-methylphenol, 2-amino-5-methylphenol, 2-amino-4-chlorophenol and/or the physiologically compatible salts thereof.

The developer component may furthermore be selected from heterocyclic developer components, such as from pyrimidine derivatives, pyrazole derivatives, pyrazolopyrimidine derivatives, or the physiologically compatible salts thereof. Preferred pyrimidine derivatives are 2,4,5,6-tetraaminopyrimidine, 4-hydroxy-2,5,6-triaminopyrimidine, and the physiologically compatible salts thereof. One preferred pyrazole derivative is 4,5-diamino-1-(2-hydroxyethyl)pyrazole and the physiologically compatible salts thereof. In particular, pyrazolo[1,5-a]pyrimidines are preferred pyrazolopyrimidines.

Preferred oxidation dye precursors of the developer type are selected from the group consisting of p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazole-1-yl)propyl]amine, N,N'-bis-(2-hydroxyethyl)-N,N'-bis-(4-aminophenyl)-1,3-diamino-propan-2-ol, bis-(2-hydroxy-5-aminophenyl)methane, 1,3-bis-(2,5-diaminophenoxy)-propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, or the physiologically compatible salts of these compounds.

Particularly preferred developer components are p-toluylenediamine, 2-(2-hydroxyethyl)-p-phenylenediamine, 2-methoxymethyl-p-phenylenediamine, N-(4-amino-3-methylphenyl)-N-[3-(1H-imidazole-1-yl)-propyl]amine, and/or 4,5-diamino-1-(2-hydroxyethyl)pyrazole, and the physiologically compatible salts thereof.

According to a further preferred embodiment of the present invention, the cosmetic agent (M1) in the container (C1) furthermore comprises at least one coupler component as an oxidation dye precursor, in addition to at least one developer component. In general, the coupler components that are used are m-phenylenediamine derivatives, naphthols, resorcinol and resorcinol derivatives, pyrazolones and m-aminophenol derivatives Preferred coupler components according to the invention are selected from:
a) m-aminophenol and the derivatives thereof, in particular 3-aminophenol, 5-amino-2-methylphenol, 3-amino-2-chloro-6-methylphenol, 5-amino-4-chloro-2-methylphenol, 5-(2'-hydroxyethyl)-amino-2-methylphenol, and 2,4-dichloro-3-aminophenol;
b) o-aminophenol and the derivatives thereof, such as 2-amino-5-ethylphenol;
c) m-diaminobenzene and the derivatives thereof, such as 2,4-diaminophenoxyethanol, 1,3-bis-(2',4'-diaminophenoxy)-propane, 1-methoxy-2-amino-4-(2'-hydroxyethylamino)benzene, 2,6-bis-(2'-hydroxyethylamino)-1-methylbenzene, 2-({3-[(2-hydroxyethyl)amino]-4-methoxy-5-methylphenyl}amino)ethanol, and 2-({3-[(2-hydroxyethyl)amino]-2-methoxy-5-methylphenyl}-amino)ethanol;
d) o-diaminobenzene and the derivatives thereof;
e) dihydroxybenzene or trihydroxybenzene derivatives, in particular resorcinol, 2-chlororesorcinol, 4-chlororesorcinol, 2-methylresorcinol, and 1,2,4-trihydroxybenzene;
f) pyridine derivatives, in particular 3-amino-2-methylamino-6-methoxypyridine, 2,6-diaminopyridine, 2,6-dihydroxy-3,4-dimethylpyridine, 2-amino-3-hydroxypyridine, and 3,5-diamino-2,6-dimethoxypyridine;
g) naphthalene derivatives, such as 1-naphthol and 2-methyl-1-naphthol;
h) morpholine derivatives, such as 6-hydroxybenzomorpholine;
i) quinoxaline derivatives;
j) pyrazole derivatives, such as 1-phenyl-3-methylpyrazole-5-on;
k) indole derivatives, such as 6-hydroxyindole;
l) pyrimidine derivatives, or
m) methylenedioxybenzene derivatives, such as 1-(2'-hydroxyethyl)-amino-3,4-methylenedioxybenzene,
and the physiologically compatible salts thereof.

Preferred coupler components according to the invention are selected from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholine-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazole-5-on, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or the physiologically compatible salts of the aforementioned compounds.

Particularly preferred coupler components according to the invention are resorcinol, 2-methylresorcinol, 4-chlororesorcinol, 5-amino-2-methylphenol, 3-aminophenol, 2-(2,4-diaminophenoxy)ethanol, 1,3-bis-(2,4-diaminophenoxy)propane, 1-methoxy-2-amino-4-(2'-hydroxyethylamino) benzene, 2-amino-3-hydroxypyridine, 2,6-dihydroxy-3,4-dimethylpyridine, 1,5-dihydroxynaphthalene, 2,7-dihydroxynaphthalene, and 1-naphthol, and the physiologically compatible salts thereof.

In a particularly preferred embodiment of the present invention, the cosmetic agents (M1) in the container (C1) are characterized by comprising, as the oxidation dye precursor, at least one developer component, selected from the group consisting of p-phenylenediamine, p-toluylenediamine, N,N-bis-(2-hydroxyethyl)amino-p-phenylenediamine, 1,3-bis-[(2-hydroxyethyl-4'-aminophenyl)amino]-propan-2-ol, 1,10-bis-(2',5'-diaminophenyl)-1,4,7,10-tetraoxadecane, 4-aminophenol, 4-amino-3-methylphenol, bis-(5-amino-2-hydroxyphenyl)methane, 2,4,5,6-tetraaminopyrimidine, 2-hydroxy-4,5,6-triaminopyrimidine, 4,5-diamino-1-(2-hydroxyethyl)-pyrazole, the physiologically compatible salts thereof, and the mixtures thereof, and at least one coupler component, selected from the group consisting of resorcinol, 2-methylresorcinol, 5-methylresorcinol, 2,5-dimethylresorcinol, 4-chlororesorcinol, resorcinol monomethyl ether, 5-aminophenol, 5-amino-2-methylphenol, 5-(2-hydroxyethyl)amino-2-methylphenol, 3-amino-4-chloro-2-methylphenol, 3-amino-2-chloro-6-methylphenol, 3-amino-2,4-dichlorophenol, 2,4-diaminophenoxyethanol, 2-amino-4-(2'-hydroxyethyl)aminoanisole sulfate, 1,3-bis-(2,4-diaminophenoxy)propane, 2-amino-3-hydroxypyridine, 2-methylamino-3-amino-6-methoxypyridine, 2,6-dihydroxy-3,4-dimethylpyridine, 3,5-diamino-2,6-dimethoxypyridine, 1-naphthol, 2-methyl-1-naphthol, 1,5-dihydroxynaphthalene, 2,7-dihydroxynaphthalene, 1-phenyl-3-methylpyrazol-5-on, 2,6-bis-[(2'-hydroxyethyl)amino]-toluene, 4-hydroxyindole, 6-hydroxyindole, 6-hydroxybenzomorpholine, the physiologically compatible salts thereof, and the mixtures thereof.

So as to yield balanced and subtle nuancing, it may also be provided within the scope of the present invention for the cosmetic agents (M1) in the container (C1) to additionally comprise at least one direct dye. Direct dyes are dyes that attach directly to the hair and require no oxidative process to develop the color. Direct dyes are usually nitrophenylene diamines, nitroaminophenols, azo dyes, anthraquinones or indophenols.

Direct dyes can be broken down into anionic, cationic and non-ionic direct dyes.

Preferred anionic direct dyes are the compounds known under the designations Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, and tetrabromophenol blue. Preferred cationic direct dyes are cationic triphenylmethane dyes, such as Basic Blue 7, Basic Blue 26, Basic Violet 2 and Basic Violet 14, and aromatic systems substituted with a quaternary nitrogen group, such as Basic Yellow 57, Basic Red 76, Basic Blue 99, Basic Brown 16 and Basic Brown 17, and HC Blue 16, as well as Basic Yellow 87, Basic Orange 31 and Basic Red 51. Preferred non-ionic direct dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-4-nitrophenol.

It is furthermore also possible to use dyes occurring in nature as direct dyes, such as red henna, neutral henna, black henna, chamomile flower, sandalwood, black tea, walnut, buckthorn bark, sage, logwood, wild madder, *catechu*, and alkanet root.

The cosmetic agent (M1) preferably comprises the direct dyes in a total amount of 0.001 to 10 wt. %, especially 0.01 to 8 wt. %, preferably 0.1 to 5 wt. %, and in particular 0.5 to 3 wt. %, based on the total weight of the cosmetic agent (M1).

The cosmetic agents (M1) in the container (C1) comprise at least specific aminated silicone polymer as the second essential component. Adding this silicone polymer results in improved nourishment, and in particular wet combability, and/or in improved chroma of color nuances.

According to a preferred embodiment of the present invention, n in the structural unit of formula (II) denotes the integer 2 or 3, and in particular the integer 2, and A denotes a branched C4 alkyl group, and in particular an isobutyl group.

It is particularly preferred according to the invention if the cosmetic agent (M1) in the container (C1) comprises at least one aminated silicone polymer of formula

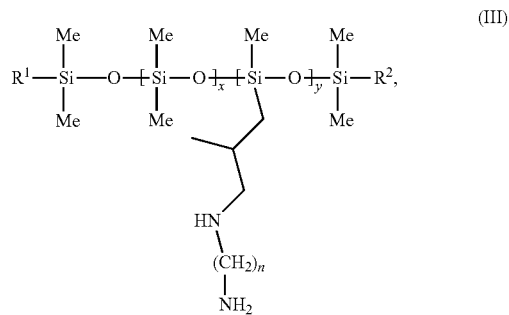

where
R1 and R2, independently of one another, denote a methyl group or a hydroxyl group;
x denotes integers from 0 to 1999, especially from 4 to 1500, preferably from 10 to 1000, more preferably from 20 to 500, and in particular from 49 to 149;

y denotes integers from 1 to 200, especially from 1 to 70, preferably from 1 to 50, more preferably from 1 to 30, and in particular from 1 to 10; and n denotes integers from 1 to 5, especially from 1 to 4, preferably from 1 to 3, and in particular 2 or 3. The use of these specific aminated silicone polymers results in increased nourishment of the keratin fibers following the alteration of the color and/or in improved chroma of color nuances.

The at least one aminated silicone polymer preferably has an average molecular weight Mw of 350 to 350,000 Da, especially of 500 to 300,000 Da, preferably of 700 to 250,000 Da, and in particular of 1,000 to 200,000 Da. Specific aminated silicone polymers having the above-described average molecular weight Mw result in particularly high nourishment of keratin fibers following the alteration of the color and/or in improved chroma of color nuances. The average molecular weight Mw can be determined by way of gel permeation chromatography, for example (Liu X. M. et. al.: "Comparative Studies of Poly(DimethylSiloxanes) Using Automated GPC-MALDI-TOF MS and On-Line GPC-ESI-TOF MS"; Am. Soc. Mass. Spectrom., 2003, 14, pages 195 to 202).

It has proven advantageous if the at least one aminated silicone polymer has an amine value above 0.25 meq/g, especially above 0.3 meq/g, and in particular above 0.4 meq/g.

It is particularly preferred within the scope of the present invention if the at least one aminated silicone polymer has an amine value of 0.25 to 5 meq/g, especially of 0.3 to 4.5 meq/g, preferably of 0.4 to 4.0 meq/g, more preferably of 0.5 to 3.0 meq/g, and in particular of 0.5 to 1.5 meq/g. The amine value denotes the milliequivalents of amine per gram of the aminofunctional silicone. This value can be determined by titration and also be described by the unit mg KOH/g. The use of aminated silicone polymers having the above-described amine values results in particularly high nourishment of keratin fibers that were colored using oxidative dyes produced from the packaging unit according to the invention. Moreover, the use of silicone polymers having amine values in the above-mentioned ranges in the cosmetic agents (M1) of the packaging unit according to the invention results in improved chroma of color nuances.

The at least one aminated silicone polymer is present in the cosmetic agent (M1) in the container (C1) in a total amount of 0.0001 to 15 wt. %, especially of 0.0005 to 10 wt. %, preferably of 0.005 to 5.0 wt. %, more preferably of 0.01 to 3.0 wt. %, and in particular of 0.05 to 1.0 wt. %, based on the total weight of the cosmetic agent (M1). The use of the above-mentioned total amount of the specific aminated silicone polymer results in increased nourishment of the keratin fibers and/or in improved chroma of color nuances.

It has been shown that adding cyclic aminated silicone polymers is particularly advantageous within the scope of the present invention. Preferred cosmetic agents (M1) according to the invention thus additionally comprise a cyclic aminated silicone polymer in a total amount of 0.003 to 1.5 wt. %, especially of 0.006 to 1.1 wt. %, preferably of 0.009 to 0.8 wt. %, more preferably of 0.01 to 0.5 wt. %, and in particular of 0.015 to 0.3 wt. %, based on the total weight of the cosmetic agent (M1), wherein the cyclic aminated silicone polymer has the formula (IV)

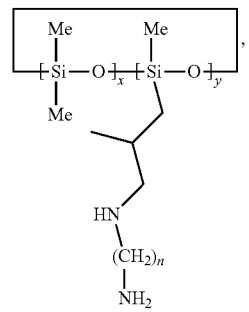
(IV)

where x denotes integers from 0 to 1999, especially from 4 to 1500, preferably from 10 to 1000, more preferably from 20 to 500, and in particular from 49 to 149; and y denotes integers from 1 to 200, especially from 1 to 70, preferably from 1 to 50, more preferably from 1 to 30, and in particular from 1 to 10. By adding aminated cyclic silicone polymers, the nourishing action and/or the chroma of color nuances of the oxidative dyes produced from the packaging unit according to the invention can be further enhanced.

Furthermore, it has proven advantageous to add dimethyl cyclosiloxanes. It is thus preferred within the scope of the present invention if the cosmetic agents (M1) additionally comprise dimethyl cyclosiloxanes in a total amount of less than 1 wt. %, based on the total weight of the cosmetic agent (M1), wherein the dimethyl cyclosiloxane has the formula (V)

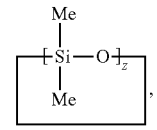
(V)

where z denotes integers from 2 to 8, especially from 2 to 6, and in particular 3, 4, 5 or 6. Adding such dimethyl cyclosiloxanes to the cosmetic agents (M1) results in a further improvement of the nourishing action and/or improvement of the chroma of color nuances.

The cosmetic agents (M1) in the container (C1) can comprise further active ingredients and additives. It is thus preferred within the scope of the present invention if the cosmetic agent (M1) additionally comprises at least one further compound, selected from the group consisting of (i) thickeners; (ii) linear or branched, saturated or unsaturated alcohols having 8 to 20 carbon atoms; (iii) surfactants, and in particular amphoteric surfactants; (iv) alkalizing agents; (v) oils; and (vi) the mixtures thereof.

The cosmetic agents (M1) in the container (C1) are preferably formulated as flowable preparations. The cosmetic agents (M1) should be formulated so as to be easy to apply to and distribute at the application site, while being sufficiently viscous enough to remain at the site of action during the residence time and not run.

It has thus proven advantageous according to the invention if the cosmetic agents (M1) comprise at least one thickener from the group of (i) anionic, synthetic polymers; (ii) cationic, synthetic polymers; (iii) naturally occurring thickeners, such as non-ionic guar gums, scleroglucan gums or xanthan gums, gum arabic, ghatti gum, karaya gum, tragacanth gum, carrageenan gum, agar-agar, locust bean gum, pectins, alginates, starch fractions and derivatives, such as amylose, amylopectin and dextrins, as well as cellulose derivatives, such as methyl cellulose, carboxyalkyl celluloses and hydroxyalkyl celluloses; (iv) non-ionic, synthetic polymers, such as polyvinyl alcohol or polyvinylpyrrolidone; (v) inorganic thickeners, in particular phyllosilicates, such as bentonite, and in particular smectite, such as montmorrillonite or hectorite; and (vi) the mixtures thereof, in a total amount of 0.0005 to 5.0 wt. %, especially of 0.001 to 3.0 wt. %, preferably of 0.005 to 1.0 wt. %, and in particular of 0.008 to 0.01 wt. %, based on the total weight of the cosmetic agent (M1).

It has proven advantageous within the scope of the present invention if the thickener present is at least one naturally occurring thickener, and in particular xanthan gum and the salts thereof, in a total amount of 0.0005 to 5.0 wt. %, especially 0.001 to 1.0 wt. %, preferably 0.005 to 0.5 wt. %, and in particular 0.01 to 0.1 wt. %, based on the total weight of the cosmetic agent (M1).

Within the scope of the present embodiment, it may furthermore be preferred if the linear or branched, saturated or unsaturated alcohol having 8 to 30 carbon atoms is selected from the group consisting of myristyl alcohol (1-tetradecanol), stearyl alcohol (1-octadecanol), cetearyl alcohol, 2-octyldodecanol, arachyl alcohol (eicosan-1-ol), gadoleyl alcohol ((9Z)-eicos-9-en-1-ol), arachidonic alcohol ((5Z,8Z,11Z,14Z)-eicosa-5,8,11,14-tetraen-1-ol), especially 2-octyldodecanol and/or cetearyl alcohol, and is present in a total amount of 1.0 to 35 wt. %, especially of 5.0 to 30 wt. %, preferably of 10 to 25 wt. %, and in particular of 12 to 20 wt. %, based on the total weight of the cosmetic agent (M1).

Furthermore, the cosmetic agents (M1) in the container (C1) can preferably comprise at least one partial ester made of a polyol having 2 to 6 carbon atoms and linear saturated carboxylic acids having 12 to 30, and in particular 14 to 22, carbon atoms, wherein the partial esters may be hydroxylated, in a total amount of 0.5 to 10 wt. %, and in particular of 3.0 to 8.0 wt. %, based on the total weight of the cosmetic agent. Such partial esters are in particular the monoesters and diesters of glycerol, or the monoesters of propylene glycol, or the monoesters and diesters of ethylene glycol, or the monoesters, diesters, triesters and tetraesters of pentaerythritol, each with linear saturated C12 to C30 carboxylic acids, which may be hydroxylated, and in particular those with palmitic and stearic acid, the sorbitan monoesters, diesters or triesters of linear saturated C12 to C30 carboxylic acids, which may be hydroxylated, and in particular those of myristic acid, palmitic acid, stearic acid or of mixtures of these fatty acids, and the methylglucose monoesters and diesters of linear saturated C12 to C30 carboxylic acids, which may be hydroxylated.

Within the scope of the present invention, it may be provided that the cosmetic agents (M1) in the container (C1) comprise at least one polyol partial ester, selected from the group consisting of glycerol monostearate, glycerol monopalmitate, glycerol distearate, glycerol dipalmitate, ethylene glycol monostearate, ethylene glycol monopalmitate, ethylene glycol distearate, ethylene glycol dipalmitate, and mixtures thereof, in particular mixtures of glycerol monostearate, glycerol monopalmitate, glycerol distearate and glycerol dipalmitate, in a total amount of 0.5 to 10 wt. %, and in particular of 3.0 to 8.0 wt. %, based on the total weight of the cosmetic agent (M1).

The use of the above-described alcohols, partial esters and polypartial esters in the cosmetic agents (M1) may in particular be preferred when the cosmetic agents (M1) are present in the form of an oil-in-water emulsion.

Furthermore, it may be provided according to the invention that the cosmetic agents (M1) in the container (C1) comprise at least one surfactant. Surfactants within the meaning of the present invention are amphiphilic (bifunctional) compounds, which are composed of at least one hydrophobic molecule part and at least one hydrophilic molecule part. A basic property of the surfactants and emulsifiers is the oriented absorption at interfaces, the aggregation into micelles, and the formation of lyotropic phases.

According to a preferred embodiment of the present invention, the cosmetic agents (M1) comprise at least one amphoteric surfactant in a total amount of 0.1 to 5.0 wt. %, and in particular of 0.2 to 2.0 wt. %, based on the total weight of the cosmetic agent (M1). Surface-active compounds that are referred to as amphoteric or zwitterionic surfactants are those that comprise at least one quaternary ammonium group and at least one —COO(—) or —SO3(-) group.

The compounds described hereafter are particularly preferred amphoteric surfactants within the scope of the present invention:

alkyl betaines having 8 to 20 carbon atoms in the alkyl group;
  amidopropyl betaines having 8 to 20 carbon atoms in the acyl group;
  sulfobetaines having 8 to 20 carbon atoms in the acyl group;
  amphoacetates or amphodiacetates having 8 to 20 carbon atoms in the acyl group.

In a particularly preferred embodiment, the surfactant present in the cosmetic agents (M1) is at least one amphoteric surfactant, selected from amidopropyl betaines having 9 to 13 carbon atoms in the acyl group, in a total amount of 0.1 to 5.0 wt. %, and in particular of 0.2 to 2.0 wt. %, based on the total weight of the cosmetic agent (M1).

Furthermore, it may be provided that the cosmetic agents (M1) comprise at least one ethoxylated non-ionic surfactant in a total amount of 0.5 to 6.0 wt. %, and in particular of 1.0 to 4.0 wt. %, based on the total weight of the cosmetic agent (M1). It has proven particularly advantageous if the ethoxylated non-ionic surfactant has an HLB value above 10, and preferably above 13. For this purpose, it is necessary for the non-ionic surfactant to have a sufficiently high degree of ethoxylation. In this context, the ethoxylated non-ionic surfactant present in the cosmetic agent (M1) is thus at least one ethoxylated surfactant having at least 12 ethylene oxide units. In addition to the appropriately ethoxylated fatty alcohols, in particular lauryl alcohol, myristyl alcohol, cetyl alcohol, stearyl alcohol, arachyl alcohol and behenyl alcohol, in particular the addition products of 20 to 60 moles ethylene oxide to castor oil and hydrogenated castor oil are particularly suited according to the invention. The at least one ethoxylated non-ionic surfactant is preferably selected from surfactants bearing the INCI names Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil and PEG-60 Hydrogenated Castor Oil, and mixtures of these substances, particularly preferably selected from Ceteth-20, Steareth-20, Ceteareth-20, Ceteth-30, Steareth-30 and Ceteareth-30.

Cosmetic agents (M1) within the scope of the present invention generally have an alkaline pH value, in particular between pH 8.0 and pH 12. These pH values are necessary to ensure that the outermost layer covered with scales (cuticle) opens up and allows the oxidation dye precursors and/or the oxidizing agent to penetrate into the hair.

The above-described pH value can preferably be set using an alkalizing agent. Within the scope of the present invention, the alkalizing agent is selected from the group consisting of (i) inorganic alkalizing agents; (ii) organic alkalizing agents; and (iii) the mixtures thereof, and is present in a total amount of 1.5 to 9.5 wt. %, especially of 2.5 to 8.5 wt. %, preferably of 3.0 to 8.0 wt. %, and in particular of 3.5 to 7.5 wt. %, based on the total weight of the cosmetic agent (M1).

Preferred inorganic alkalizing agents are selected from the group consisting of ammonia or ammonium hydroxide, which is to say aqueous solutions of ammonia, sodium hydroxide, potassium hydroxide, calcium hydroxide, barium hydroxide, sodium phosphate, potassium phosphate, sodium silicate, potassium silicate, sodium carbonate and potassium carbonate, and mixtures thereof. Ammonia or ammonium hydroxide is a particularly preferred alkalizing agent. Ammonia is particularly preferably present in a total amount of 0.1 to 20 wt. %, especially 0.5 to 10 wt. %, and in particular 1.0 to 7.0 wt. %, based on the total weight of the cosmetic agent (M1).

Preferred organic alkalizing agents are selected from at least one alkanolamine. Alkanolamines that are preferred according to the invention are selected from alkanolamines composed of primary, secondary or tertiary amines having a C2-C6 alkyl basic structure, which carries at least one hydroxyl group. Particularly preferred alkanolamines are selected from the group consisting of 2-aminoethan-1-ol (monoethanolamine), 3-aminopropan-1-ol, 4-aminobutan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methyl-propanol, 2-amino-2-methylbutanol, 3-amino-2-methylpropan-1-ol, 1-amino-2-methylpropan-2-ol, 3-aminopropan-1,2-diol, 2-amino-2-methylpropan-1,3-diol, 2-amino-2-ethyl-1,3-propanediol, N,N-dimethylethanolamine, triethanolamine, diethanolamine and triisopropanolamine. Especially particularly preferred alkanolamines according to the invention are selected from the group consisting of 2-aminoethan-1-ol (monoethanolamine), 2-amino-2-methylpropan-1-ol, 2-amino-2-methyl-propan-1,3-diol, and triethanolamine. Particularly preferred cosmetic agents (M1) comprise a mixture of monoethanolamine and 2-amino-2-methylpropan-1-ol. The at least one alkanolamine is preferably present in a total amount of 0.05 to 15 wt. %, especially 0.5 to 10 wt. %, and in particular 3.5 to 7.5 wt. %, based on the total weight of the cosmetic agent (M1).

Further preferred organic alkalizing agents according to the invention are selected from the basic amino acids, and particularly preferably are selected from the group consisting of L-arginine, D-arginine, D/L-arginine, L-lysine, D-lysine, D/L-lysine, and mixtures thereof. Particularly preferred basic amino acids according to the invention are selected from L-arginine, D-arginine and D/L-arginine. Preferred cosmetic agents (M1) comprise at least one alkalizing agent different from alkanolamines and ammonia in a total amount of 0.05 to 5.0 wt. %, and in particular of 0.5 to 3.0 wt. %, based on the total weight of the cosmetic agent (M1).

It is preferred according to the invention if the alkalizing agent is selected from the group consisting of sodium hydroxide, potassium hydroxide, ammonia, monoethanolamine and 2-amino-2-methylpropane, preferably monoethanolamine, and is present in a total amount of 1.5 to 9.5 wt. %, especially of 2.5 to 8.5 wt. %, preferably of 3.0 to 8.0 wt. %, and in particular of 3.5 to 7.5 wt. %, based on the total weight of the cosmetic agent (M1).

In a particularly preferred embodiment, the cosmetic agents (M1) comprise a mixture of at least two different alkanolamines, and in particular monoethanolamine and 2-amino-2-methylpropan-1-ol, serving as the alkalizing agent, in a total amount of 0.05 to 15 wt. %, especially of 0.5 to 10 wt. %, and in particular of 3.5 to 7.5 wt. %, based on the total weight of the cosmetic agent (M1).

Preferably, the pH value of the cosmetic agents (M1), measured at 22° C., is 8 to 13, especially 9.5 to 12, preferably 10 to 11.5, and in particular 10.5 to 11.

Within the scope of the present invention, it may furthermore be preferred if the cosmetic agents (M1) comprise at least one oil, selected from the group consisting of sunflower oil, corn oil, soy bean oil, pumpkin seed oil, grape seed oil, sesame oil, hazelnut oil, apricot kernel oil, macadamia nut oil, arara oil, castor oil, avocado oil, and the mixtures thereof, in a total amount of 0.1 to 10 wt. %, preferably of 0.2 to 5.0 wt. %, and in particular of 0.5 to 2.0 wt. %, based on the total weight of the cosmetic agent (M1). Using at least one of the above-mentioned oils can further enhance the nourishing effect of the aminated silicon polymers.

The cosmetic agents (M1) particularly preferably comprise grape seed oil in a total amount of 0.1 to 10 wt. %, especially 0.2 to 5.0 wt. %, and in particular 0.5 to 2.0 wt. %, based on the total weight of the cosmetic agent (M1).

According to a particularly preferred embodiment of the present invention, the cosmetic agents (M1) in the container (C1) present in the form of an oil-in-water emulsion comprise, based on the total weight of the cosmetic agents (M1), octyldodecanol in a total amount of 2.0 to 20 wt. %, and in particular of 5.0 to 12 wt. %; furthermore mixtures of glycerol monostearate, glycerol monopalmitate, glycerol distearate and glycerol dipalmitate in a total amount of 0.5 to 10 wt. %, and preferably 3.0 to 8.0 wt. %; furthermore at least one amphoteric surfactant, selected from amidopropyl betaines having 9 to 13 carbon atoms in the acyl group, in a total amount of 0.1 to 5.0 wt. %, and in particular of 0.2 to 2.0 wt. %; furthermore a mixture of at least two different alkanolamines, and in particular monoethanolamine and 2-amino-2-methylpropan-1-ol in a total amount of 0.05 to 15 wt. %, especially of 0.5 to 10 wt. %, and in particular of 3.5 to 7.5 wt. %; furthermore grape seed oil in a total amount of 0.1 to 10 wt. %, preferably 0.2 to 5.0 wt. %, and in particular 0.5 to 2.0 wt. %.

The container (C2) of the packaging unit according to the invention comprises an oxidizing agent preparation (M2), which comprises at least one oxidizing agent.

The oxidizing agents within the scope of the present invention are different from atmospheric oxygen. Oxidizing agents that can be used in the oxidizing agent preparation (M2) are hydrogen peroxide and the solid addition products thereof to organic and inorganic compounds. Solid addition products that may be used according to the invention include in particular the addition products to urea, melamine, polyvinylpyrrolidone and sodium borate. Hydrogen peroxide and/or one of the solid addition products thereof to organic or inorganic compounds are particularly preferred oxidizing agents. According to the invention, the oxidizing agent is thus preferably selected from the group consisting of persulfates, chlorites, hydrogen peroxide and addition products of hydrogen peroxide to urea, melamine and sodium borate, and in particular hydrogen peroxide.

A particularly preferred embodiment of the present invention is thus characterized in that hydrogen peroxide is present, serving as the oxidizing agent, in a total amount of 0.5 to 20 wt. %, especially 2.0 to 15 wt. %, preferably 3.0 to 12 wt. %, more preferably 4.0 to 10 wt. %, and in particular 5.5 to 9.0 wt. %, based on the total weight of the oxidizing agent preparation (M2). The calculation of the total amount is based on 100% H2O2.

The oxidizing agent preparations (M2) in the container (C2) can furthermore comprise water in a total amount of 40 to 98 wt. %, and in particular of 65 to 85 wt. %, based on the total weight of the oxidizing agent preparation (M2).

According to a preferred embodiment of the present invention, the oxidizing agent preparations (M2) furthermore comprise at least one linear saturated alkanol having 12 to 30 carbon atoms, and in particular having 16 to 22 carbon atoms, in a total amount of 0.1 to 10 wt. %, especially of 0.5 to 5.0 wt. %, and in particular of 1.0 to 4.0 wt. %, based on the total weight of the oxidizing agent preparation (M2). In particular, cetyl alcohol, stearyl alcohol, arachidyl alcohol, behenyl alcohol and lanolin alcohol, or mixtures of these alcohols, as they can be obtained during the large-scale hydrogenation of vegetable and animal fatty acids, and mixtures of these alkanols, are preferred. The cetearyl alcohol mixture is particularly preferred.

In a further preferred embodiment of the present invention, the oxidizing agent preparations (M2) comprise at least one ethoxylated non-ionic surfactant, which is preferably selected from surfactants bearing the INCI names Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil and PEG-60 Hydrogenated Castor Oil, and mixtures of these substances, particularly preferably selected from Ceteth-20, Steareth-20, Ceteareth-20, Ceteth-30, Steareth-30 and Ceteareth-30, in a total amount of 0.1 to 10 wt. %, especially of 0.5 to 5.0 wt. %, and in particular of 1 to 4.0 wt. %, based on the total weight of the oxidizing agent preparation (M2).

Within the scope of the present invention, it may furthermore be provided that the oxidizing agent preparations (M2) comprise at least one ester of a carboxylic acid having 10 to 20 carbon atoms and a linear or branched alcohol having 1 to 5 carbon atoms, in particular isopropyl myristate, in a total amount of 3.0 to 25 wt. %, especially of 5.0 to 20 wt. %, and in particular of 8.0 to 15 wt. %, based on the total weight of the oxidizing agent preparation (M2).

According to a particularly preferred embodiment of the present invention, the oxidizing agent preparations (M2) in the container (C2) comprise, based on the total weight of the oxidizing agent preparations (M2),
- at least one linear saturated alkanol having 12 to 30 carbon atoms in a total amount of 0.1 to 10 wt. %, especially of 0.5 to 5.0 wt. %, and in particular 1.0 to 4.0 wt. %; furthermore
- at least one ethoxylated non-ionic surfactant, which is preferably selected from surfactants bearing the INCI names Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil and PEG-60 Hydrogenated Castor Oil, and mixtures of these substances, particularly preferably selected from Ceteth-20, Steareth-20, Ceteareth-20, Ceteth-30, Steareth-30 and Ceteareth-30, in a total amount of 0.1 to 10 wt. %, especially of 0.5 to 5.0 wt. %, and in particular of 1.0 to 4.0 wt. %; and
- at least one ester of a carboxylic acid having 10 to 20 carbon atoms and a linear or branched alcohol having 1 to 5 carbon atoms, preferably isopropyl myristate, in a total amount of 3.0 to 25 wt. %, especially of 5.0 to 20 wt. %, and in particular of 8.0 to 15 wt. %.

The oxidizing agent preparations (M2) according to the invention furthermore comprise at least one acid. Preferred acids are selected from dipicolinic acid, food grade acids such as citric acid, acetic acid, malic acid, lactic acid and tartaric acid, diluted mineral acids such as hydrochloric acid, phosphoric acid, pyrophosphoric acid and sulfuric acid, and mixtures thereof. The oxidizing agent preparations preferably have a pH value in the range of 2 to 5, and in particular of 3 to 4.

So as to produce oxidative dye compositions from the packing unit (kit of parts) according to the invention, the cosmetic agent (M1) in the container (C1) is mixed with the oxidizing agent preparation (M2) in the container (C2), or vice versa.

Furthermore, it may be particularly advantageous according to the invention when the packaging unit according to the invention comprises at least one further hair treatment agent, and in particular a conditioning agent preparation, in an additional container. This conditioning agent preparation advantageously comprises at least one conditioning agent selected from the group consisting of cationic polymers, silicone derivatives, and oils. The packaging unit can moreover comprise application aids, such as combs, applicettes or brushes, personal protective clothing, in particular disposable gloves, and optionally usage instructions. An applicette shall be understood to mean a wide brush, having a tip at the handle end which allows and simplifies the process of separating bundles of fibers or strands of hair from the total amount of fibers.

A further subject matter of the present invention is a method for coloring, and in particular lightening, keratin fibers, wherein the method comprises the following method steps:
a) providing a packaging unit (kit of parts) according to the invention;
b) mixing the cosmetic agent (M1) and the oxidizing agent preparation (M2) present in the packaging unit according to the invention;
c) applying the mixture obtained in step c) onto the keratin fibers, and leaving this mixture on the keratin fibers for a period of 10 to 60 minutes, and preferably of 20 to 45 minutes, at room temperature and/or at least at 30° C.;
d) rinsing the keratin fibers with water and/or a cleaning composition for 1 to 5 minutes; and
e) optionally applying a post-treatment agent onto the keratin fibers and rinsing after a period of 1 to 10 minutes.

The method according to the invention for coloring keratin fibers using a specific aminated silicone polymer results in improved nourishment of dyed keratin fibers and/or in improved chroma of color nuances.

Within the scope of the present invention, room temperature shall be understood to mean the ambient temperature that prevails without the application of external heat and is preferably 10 to 39° C. The action of the coloring composition may be increased by supplying external heat, for example by way of a hood dryer. The preferred residence duration of the coloring composition on the keratin fibers is 10 to 60 min, and preferably 20 to 45 min. After the residence duration has ended, the remaining dye is washed out of the keratin fibers using a cleaning composition, which preferably comprises at least one cationic and/or anionic and/or non-ionic surfactant, and/or water. The procedure is optionally repeated with another agent. After the dye has been washed out, the keratin fibers are optionally rinsed with a post-treatment agent, such as a conditioning agent, and dried by way of a towel or a hot air blower. The user typically applies the coloring composition using his or her hand. During this process, personal protective clothing is preferably worn, in particular suitable protective gloves, made of plastic or latex for single use (disposable gloves), for example, and optionally an apron. However, it is also possible to apply the dyes onto the keratin fibers using an application aid.

Particularly preferred methods according to the invention are characterized in that the methods result in improved nourishment and/or chroma of color nuances. By using at least one specific aminated silicone polymer, the nourishment and/or chroma of color nuances resulting from the method according to the invention are greater than the nourishment and/or chroma of color nuances that can be achieved in the absence of the aminated silicone polymer b) used within the scope of the present invention.

What was said with respect to the packaging unit according to the invention applies, mutatis mutandis, with respect to the cosmetic agents (M1) and the oxidizing agent preparation (M2) used within the scope of the method according to the invention, and further preferred embodiments of the method according to the invention.

Finally, a further subject matter of the present invention is the use of a packaging unit according to the invention for producing a cosmetic agent for altering the color of keratin fibers, providing increased nourishment of the keratin fibers and/or improved chroma of color nuances. The use of a specific aminated silicone polymer results in increased nourishment of dyed keratin fibers and/or in improved chroma of color nuances.

What was said with respect to the packaging unit according to the invention and with respect to the method according to the invention applies, mutatis mutandis, with respect to further preferred embodiments of the use according to the invention.

The following examples are intended to describe preferred embodiments of the invention, without limiting the invention.

Examples

1. Formulations

Compositions of the cosmetic agents (M1) used (oil-in-water emulsions, all amounts in wt. %). The aminated silicone polymer used in the following formulations is preferably a silicone polymer of formula (III), where n=2 or 3 and the average molecular weight Mw is 1,000 to 200,000 Da.

| Raw material | V1 | E1* | E2* |
| --- | --- | --- | --- |
| Xanthan gum | 0.05 | 0.05 | 0.05 |
| 2-octyldodecanol | 2.3 | 2.3 | 2.3 |
| Lanette N$^{a)}$ | 14 | 14 | 14 |
| Cetearyl alcohol | 3.9 | 3.9 | 3.9 |
| Glycerol monostearate | 6.0 | 6.0 | 6.0 |
| Glycerol 99.5% | 2.0 | 2.0 | 2.0 |
| Cocoamidopropyl betaine, 40% | 2.0 | 2.0 | 2.0 |
| Monoethanolamine | 4.5 | 4.5 | 4.5 |
| 2-amino-2-methylpropanol | 0.1 | 0.1 | 0.1 |
| Sodium sulfite, anhydrous | 0.2 | 0.2 | 0.2 |
| Caramel syrup, 75% | 0.1 | 0.1 | 0.1 |
| Grape seed oil | 1.0 | 1.0 | 1.0 |
| p-toluylene diamine sulfate | 0.03 | 0.03 | 0.03 |
| 4-amino-3-methylphenol | 0.3 | 0.3 | 0.3 |
| 1,3-benzenediol | 0.04 | 0.04 | 0.04 |
| 1-naphthol | 0.09 | 0.09 | 0.09 |
| 5-amino-2-methylphenol | 0.2 | 0.2 | 0.2 |
| 2-amino-6-chloro-4-nitrophenol | 0.2 | 0.2 | 0.2 |
| aminated silicone polymer** | — | 0.97 | 1.9 |
| Water, deionized | to make up to 100.00 | to make up to 100.00 | to make up to 100.00 |

*according to the invention
**active substance
$^{a)}$INCI name: Cetearyl alcohol, Sodium cetearyl sulfate (BASF)

The fat base was melted in each case at 80° C. and dispersed with a portion of the water. Thereafter, the remaining components of the composition were consecutively incorporated while stirring. Then water was added to make 100 wt. %, and the composition was stirred until cold. Composition V1 is a comparative composition not according to the invention, comprising no aminated silicone polymer. Compositions E1 and E2 are examples according to the invention.

Oxidizing agent preparation O1 (all amounts in wt. %)

| Raw material | O1 |
| --- | --- |
| Disodium pyrophosphate | 0.10 |
| Dipicolinic acid | 0.10 |
| Potassium hydroxide 50% | 0.22 |
| 1-hydroxyethane-1,1-diphosphonic acid 60% | 0.25 |
| Emulgade F$^{b)}$ | 4.0 |
| Cetearyl alcohol | 0.5 |
| Ceteareth-20 | 0.5 |
| Beeswax | 0.3 |
| Isopropyl myristate | 10 |
| Hydrogen peroxide 50% | 11.2 |
| Water, deionized | to make up to 100 |

$^{b)}$INCI name: Cetearyl alcohol, PEG-40 Castor oil, Sodium cetearyl sulfat (BASF)

2. Improved nourishment as a result of the addition of at least one specific aminated silicone polymer.

So as to produce the oxidative dyes for determination of the nourishment, the cosmetic agents V1, E1 and E2 were each mixed with the above oxidizing agent preparation O1 using a weight ratio of 1:1.

12 strands of natural light-brown European hair (IHIP (New York), lot #03/2012, N104, length 15 cm, weight 1 g) were washed with an aqueous sodium laureth sulfate solution (3% active substance content in the solution). The strands were dried by exposure to air and stored for 24 hours at 25° C. and 25% relative humidity. After soaking these strands in water for 5 minutes, the wet combability thereof was determined (reference value).

For the colorations, 12 strands of natural European hair (IHIP (New York), lot #03/2012, N104, length 15 cm, weight 1 g) were used for each oxidative dye. For this purpose, 4 g of the previously produced oxidative dyes were applied in each case per 1 g of strand of hair. After the strands had been dyed for 30 min at 32° C., they were rinsed with water for 2 min and dried by exposure to air.

The measurement of the wet combability was carried out as follows: Prior to the measurement, each strand was moistened for 2 seconds with water while combing with a hard rubber comb (Hercules Sägemann, Hamburg Germany). After having carried out 3 combing processes, the combing force is measured during 10 more combing processes, wherein the respective strand of hair is slowly rotated during the combing process. The measured values obtained are compared using the following statistical tests embedded in the software Statistica 10.0 (StatSoft Inc., USA)

Shapiro-Wilk test (test for normal distribution)
Grubbs' outlier test
Bartlett test (test of homoscedasticity of variances)
Univariate significance test
Newman-Keuls test (determination of significant differences)
Unequal N HSD test (test for multiple comparisons).

The change in the combing force dK in percent can be calculated using the formula $dK=[(K0-Ki)/KO]*100$. KO is the mean value of the combing force of the undyed strands of hair, and Ki is the mean value of the strands of hair treated with the respective oxidative dye.

The lower the applied combing force, and thus the higher the change in the combing force, the higher is the nourishment of the strands of hair. Table 2 shows the dK values for the colorations using the cosmetic agents V1, E1 and E2. The colorations using the cosmetic agents E1 and E2 according to the invention, which comprise at least one specific aminated silicone polymer in a total amount of 0.97 wt. % and 1.9 wt. %, respectively, exhibit a higher change in combing force, and thus increased nourishment, compared to the colorations using no aminated silicone polymer (V1).

| Oxidative dye | dK [%] |
|---|---|
| V1 + O1 (1:1) | 36 |
| E1 + O1 (1:1) | 48 |
| E2 + O1 (1:1) | 54 |

3. Improved chroma of color nuances as a result of the addition of at least one specific aminated silicone polymer So as to produce the oxidative dyes for determination of the chroma and color depth, the cosmetic agents V1, E1 and E2 were each mixed with the above oxidizing agent preparation O1 using a weight ratio of 1:1.

The oxidative dyes thus produced were each applied in a defined amount (4 g oxidative dye per 1 g yak hair) onto strands of yak hair (in each case 12 strands per oxidative dye), and remained on the strands of hair for a residence duration of 30 minutes at 32° C. Afterwards, the remaining agents were each rinsed from the strands of hair for 2 minutes with lukewarm water, the strands were first dried with a towel and then blow-dried (colorations: bright red).

All strands were measured by way of a colorimeter from Datacolor, type Spectraflash 450. The dC value used for the assessment of the chroma is derived from the a*b color readings measured on the respective strand as follows:

$$dC=[(ai-aO)2+(bi-bO)2]1/2$$

Here, aO and bO are each the mean values of the color readings of the untreated strands of yak hair ascertained from the 12 measurements, while and bi represent the mean values of the color readings after oxidatively dyeing the strands of hair using the respective oxidative dye.

One indicator of the intensity of the colorations is the chroma. The higher the dC value, the higher is the intensity of the nuance. The table below shows the dC values for the colorations using the cosmetic agents V1, E1 and E2. The colorations using the cosmetic agents E1 and E2 according to the invention, which comprise at least one specific aminated silicone polymer in a total amount of 0.97 wt. % and 1.9 wt. %, respectively, exhibit improved intensity compared to the colorations using no aminated silicone polymer (V1).

| Oxidative dye | dC |
|---|---|
| V1 + O1 (1:1) | 38.74 |
| E1 + O1 (1:1) | 41.04 |
| E2 + O1 (1:1) | 39.50 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

The invention claimed is:

1. A packaging unit (kit of parts) for dyeing keratin fibers, comprising, formulated separately from one another, a) at least one container (C1), comprising a cosmetic agent (M1), which comprises at least one compound, selected from the group consisting of oxidation dye precursors, direct dyes and the mixtures thereof, and at least one aminated silicone polymer, comprising at least one structural unit of formula (I) and at least one structural unit of formula (II)

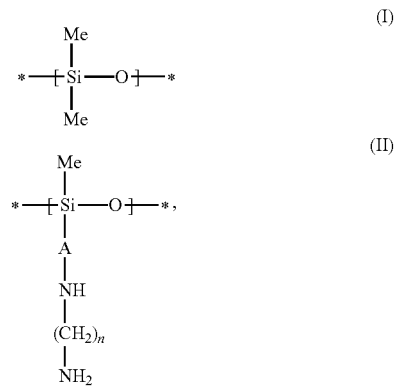

where
A denotes a linear or branched $C_4$ to $C_8$ alkyl group; and
n denotes integers from 1 to 4, and
a cyclic aminated silicone polymer in a total amount of 0.003 to 1.5 wt. % based on the total weight of the cosmetic agent, wherein the cyclic aminated silicone polymer has the formula (IV)

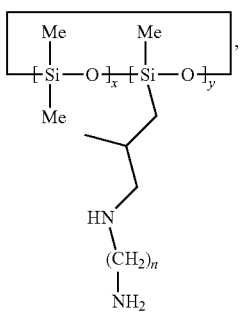
(IV)

where x denotes integers from 0 to 1999; and y denotes integers from 1 to 200 b) at least one container (C2), comprising an oxidizing agent preparation (M2), which, in a cosmetically compatible carrier, comprises at least one oxidizing agent in a total amount of 0.5 to 15 wt. % based on the total weight of the oxidizing agent preparation.

2. The packaging unit according to claim 1, characterized in that n in the structural unit of formula (II) denotes the integer 2 or 3, and A denotes a branched $C_4$ alkyl group.

3. The packaging unit according to claim 1, wherein the cosmetic agent (M1) in the container (C1) comprises at least one aminated silicone polymer of formula (III)

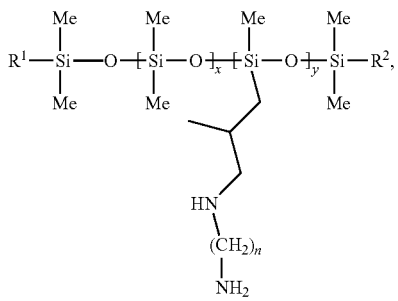
(III)

where $R^1$ and $R^2$, independently of one another, denote a methyl group or a hydroxyl group; x denotes integers from 0 to 1999; and n denotes integers from 1 to 5.

4. The packaging unit according to claim 1, wherein the at least one aminated silicone polymer has an average molecular weight $M_W$ of 350 to 350,000 Da.

5. The packaging unit according to claim 1, wherein the at least one aminated silicone polymer has an average molecular weight $M_W$ of 1,000 to 200,000 Da.

6. The packaging unit according to claim 1, wherein the at least one aminated silicone polymer has an amine value of 0.25 to 5 meq/g.

7. The packaging unit according to claim 1, wherein the at least one aminated silicone polymer has an amine value of 0.5 to 1.5 meq/g.

8. The packaging unit according to claim 1, wherein the cosmetic agent (M1) in the container (C1) comprises the at least one aminated silicone polymer in a total amount of 0.0001 to 15 wt. % based on the total weight of the cosmetic agent (M1).

9. The packaging unit according to claim 1, wherein the cosmetic agent (M1) in the container (C1) comprises the at least one aminated silicone polymer in a total amount of 0.05 to 1.0 wt. % based on the total weight of the cosmetic agent (M1).

10. The packaging unit according to claim 1, wherein the cosmetic agent (M1) additionally comprises dimethyl cyclosiloxanes in a total amount of less than 1 wt. %, based on the total weight of the cosmetic agent (M1), wherein the dimethyl cyclosiloxane has the formula (V)

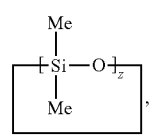
(V)

where z denotes integers from 2 to 8.

11. The packaging unit according to claim 1, wherein the cosmetic agent (M1) additionally comprises at least one further compound selected from the group consisting of (i) thickeners; (ii) linear or branched, saturated or unsaturated alcohols having 8 to 20 carbon atoms; (iii) surfactants; (iv) alkalizing agents; (v) oils; and (vi) the mixtures thereof.

12. The packaging unit according to claim 11, wherein the alkalizing agent present is a mixture of at least two different alkanolamines in a total amount of 0.05 to 15 wt. % based on the total weight of the cosmetic agent (M1).

13. The packaging unit according to claim 11, wherein the alkalizing agent present is a mixture of monoethanolamine and 2-amino-2-methylpropan-1-ol in a total amount of 0.5 to 10 wt. % based on the total weight of the cosmetic agent (M1).

14. The packaging unit according to claim 11, wherein the alkalizing agent present is a mixture of monoethanolamine and 2-amino-2-methylpropan-1-ol in a total amount of 3.5 to 7.5 wt. % based on the total weight of the cosmetic agent (M1).

15. The packaging unit according to claim 1, wherein the oxidizing agent is selected from the group consisting of: persulfates, chlorites, hydrogen peroxide and addition products of hydrogen peroxide to urea, melamine and sodium borate.

16. The packaging unit according to claim 1, wherein the oxidizing agent is hydrogen peroxide.

17. A method for coloring keratin fibers, comprising:
a) providing a packaging unit (kit of parts) according to claim 1;
b) mixing the cosmetic agent (M1) and the oxidizing agent preparation (M2) present in the packaging unit according to claim 1;
c) applying the mixture obtained in step c) onto the keratin fibers, and leaving this mixture on the keratin fibers for a period of 10 to 60 minutes, at room temperature and/or at least at 30° C.;
d) rinsing the keratin fibers with water and/or a cleaning composition for 1 to 5 minutes; and
e) optionally applying a post-treatment agent onto the keratin fibers and rinsing after a period of 1 to 10 minutes.

18. The method according to claim 16, wherein the method results in improved nourishment and/or chroma of color nuances.

* * * * *